United States Patent
Brewer et al.

(10) Patent No.: US 7,122,171 B2
(45) Date of Patent: Oct. 17, 2006

(54) SUPRAMOLECULAR COMPLEXES AS PHOTOCATYLYSTS FOR THE PRODUCTION OF HYDROGEN FROM WATER

(75) Inventors: Karen J. Brewer, Blacksburg, VA (US); Mark Elvington, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 67 days.

(21) Appl. No.: 11/091,901

(22) Filed: Mar. 29, 2005

(65) Prior Publication Data

US 2006/0120954 A1   Jun. 8, 2006

(51) Int. Cl.
*C01B 3/08*   (2006.01)
(52) U.S. Cl. ..................................... 423/657
(58) Field of Classification Search ............. None
See application file for complete search history.

(56) References Cited

U.S. PATENT DOCUMENTS

2003/0170171 A1*   9/2003   Cortright et al. ........ 423/648.1
2003/0180767 A1*   9/2003   Brewer et al. ................. 435/6
2005/0232856 A1*   10/2005   Stevens et al. ............. 423/651
2005/0232858 A1*   10/2005   Hampden-Smith et al. . 423/652

OTHER PUBLICATIONS

Peng, Xiaojun et al. "New oxygen-evolving complexes in artificial photosynthesis system splitting water into oxygen and hydrogen." Preprints of Symposia-American Chemical Society, Division of Fuel Chemistry (2004), 49(2); pp. 974-975.*
Amouyal, Edmond. "Water splitting: from molecular to supramolecular photochemical systems." Homogeneous Photocatalysis, Wiley Series in Photoscience and Engineering, Apr. 1997; 426 pages.*
Cecal, Al. et al. "On hydrogen production by catalytic split of water." Analele Siintifice ale Universitatii, vol. 9, 2001; pp. 15-20.*
Cecal, Alexandru et al. "Radiolytic splitting of water molecules in the presence of some supramolecular compounds." Jouranl of the Serbian Chemical Society, vol. 68(7), 2003, pp. 593-598.*

* cited by examiner

*Primary Examiner*—Colleen P. Cooke
*Assistant Examiner*—Paul Wartalowicz
(74) *Attorney, Agent, or Firm*—Whitham, Curtis, Christofferson & Cook, PC

(57) ABSTRACT

Supramolecular complexes designed to produce hydrogen from water are provided. The supramolecular complexes absorb visible light and undergo charge transfer, leading to the collection of electrons at a reactive metal center, where the electrons reduce water to hydrogen. The complex remains intact during electron collection and hydrogen production.

7 Claims, 14 Drawing Sheets

Terminal Ligands 2,2' - bipyridine (bpy)

1,10-phenanthroline (phen)

2,2',6'2''-terpyridine (tpy)

Bridging Ligands 2,3'-bis(2-pyridyl)pyrazine (dpp)

2,2'-bipyrimidine (bpm)

H₂O

Expose to
supramolecular complex

Expose to a source of
radiant energy

H₂

US 7,122,171 B2

SUPRAMOLECULAR COMPLEXES AS PHOTOCATYLYSTS FOR THE PRODUCTION OF HYDROGEN FROM WATER

CROSS REFERENCE TO RELATED APPLICATIONS

This application is related to U.S. patent application Ser. No. 10/355,258, filed Jan. 31, 2003, and to U.S. provisional patent application Ser. No. 60/352,865 filed Feb. 1, 2002, and to U.S. provisional patent application Ser. No. 60/632,339, filed Dec. 2, 2004, the complete contents of which is herein incorporated by reference.

BACKGROUND OF THE INVENTION

1. Field of the Invention

The invention generally relates to supramolecular complexes designed to convert light energy into chemical energy. Specifically, these supramolecular complexes produce hydrogen from water. The conversion of light energy into chemical energy could occur using other chemical feedstocks, for example, the reduction of carbon dioxide. In particular, the invention provides supramolecular complexes that absorb visible light and undergo charge transfer, leading to the collection of electrons at a reactive metal center, and the reduction of water to hydrogen.

2. Background of the Invention

The multi-electron reduction of substrates is a key area of research, especially as it relates to energy production, light to energy conversion, and water splitting. The splitting of water is an energetically uphill process, but one that can thermodynamically be accomplished through the use of solar energy. The relevant equations for water splitting are:

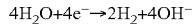

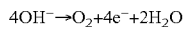

Therefore, for even the production of only one hydrogen molecule, a multi-electron process is necessary. One of the major impediments to the efficient conversion of solar energy is a need for an understanding of multi-electron catalysis.

The area of supramolecular chemistry seems an ideal forum in which to study multi-electron chemistry[1], especially using covalently linked ruthenium charge transfer chromophores[2]. Nocera[3] recognized the importance of these multi-electron processes and recently made significant progress in this area using multi-metallic complexes. The design of a functioning device for photoinitiated electron collection within a single molecular unit has been described.[4] It was shown that $\{[(bpy)_2Ru(dpb)]_2IrCl_2\}(PF_6)_5$ (bpy=2,2'-bipyridine and dpb=2,3-bis(2-pyridyl)benzoquinoxaline) was able, through a series of steps, and two single photon excitations, to become doubly reduced, storing the electrons on the $\pi^*$ orbitals of the dpb bridging ligand. Only one other report has shown photoinitiated electron collection in a molecular system that remains intact following electron collection.[5] The systems reported by MacDonnell and Campagna use bridging ligands with an extended structure in which the spectroscopic orbital for the metal to ligand charge transfer (MLCT) transition is different than the lowest lying acceptor orbital, allowing for the functioning of these promising systems. One common feature of these successful systems is that the orbital accepting the first optically populated electron is different from the orbital that is involved in the second optical excitation. This feature of these functioning systems is maintained in all the proposed Rh centered systems. Bocarsly reported an interesting approach to photoinitiated electron collection in which the fragmentation of the supramolecular assembly following electron collection serves as a driving force for this reaction.[6,7] Bocarsly has exploited an unstable $Pt^{III}$ redox state in $[(CN)_5Fe^{II}(CN)Pt^{IV}(NH_3)_4(NC)Fe^{II}(CN)_5]^{4-}$ and related systems to lead to electron collection at a metal leading to complex fragmentation. Bocarsly showed excitation of the metal to metal charge transfer (MMCT) state directly leads to a net two electron charge transfer that dissociates the complex into two $Fe^{III}$ and one $Pt^{II}$ species.

Few molecular systems exist that successfully use light energy to collect electrons. There is thus an ongoing need for the discovery of molecular systems capable of electron collection, particularly when the systems utilize the electrons to carry out useful catalytic reactions such as splitting of $H_2O$ to produce $H_2$, and particularly when the molecular systems remain intact following electron collection.

SUMMARY OF THE INVENTION

The present invention provides mixed-metal supramolecular complexes capable of photoinitiated electron collection, and able to catalyze the production of hydrogen from water. These systems are also applicable for conversion of solar energy into chemical energy via the reduction of other substrates. These substrates could include carbon containing material like carbon dioxide or carbon monoxide. The supramolecular complexes are unique in that the electrons are collected on a metal center and the complex remains intact following electron collection. Interestingly, the photoreduced complexes also possess the ability to be further reduced (on the p* system of the bridging ligands, described below). This ability to undergo further photoreduction provides additional electrons, or electrons with a higher potential available, for the reduction of the substrate, i.e. water to hydrogen.

It is an object of this invention to provide a method of producing hydrogen from water. The method comprises the step of exposing water to a supramolecular complex and a source of radiant energy. The supramolecular complex comprises: at least one metal to ligand charge transfer (MLCT) light absorbing metal; at least one bridging $\pi$-acceptor ligand; at least one electron acceptor metal; and at least one terminal ligand. The step of exposing results in production of hydrogen from the water. In one embodiment, the MLCT light absorbing metal is ruthenium. In one embodiment, the bridging $\pi$-acceptor ligand is 2,3'-bis(2-pyridyl)pyrazine. In one embodiment, the electron acceptor metal is rhodium. In one embodiment, the terminal ligand is 2,2'-bipyridine. In a preferred embodiment, the supramolecular complex is $[(bpy)_2Ru(dpp)RhCl_2(dpp)Ru(bpy)_2]^{5+}$. A distinguishing feature of the method is that the supramolecular complex remains intact during this process.

The invention also provides a system for reducing water to produce hydrogen. The system comprises a vessel for containing water and a supramolecular complex, and means for directing radiant energy towards the vessel or for exposing the vessel to radiant energy, so that the radiant energy interacts with the supramolecular complex, which reduces water in the vessel to produce hydrogen. The supramolecular complex comprises: at least one metal to ligand charge transfer (MLCT) light absorbing metal; at least one bridging $\pi$-acceptor ligand; at least one electron acceptor metal; and at least one terminal ligand.

In one embodiment, the MLCT light absorbing metal is ruthenium. In one embodiment, the bridging π-acceptor ligand is 2,3'-bis(2-pyridyl)pyrazine. In one embodiment, the electron acceptor metal is rhodium. In one embodiment, the terminal ligand is 2,2'-bipyridine. In a preferred embodiment, the supramolecular complex is [(bpy)$_2$Ru(dpp)RhCl$_2$(dpp)Ru(bpy)$_2$]$^{5+}$. A distinguishing feature of the method is that the supramolecular complex remains intact during the production of hydrogen from water.

DETAILED DESCRIPTION OF THE PREFERRED EMBODIMENTS OF THE INVENTION

The present invention provides supramolecular systems or complexes capable of undergoing photoinitiated multi-electron processes. The supramolecular complexes are capable of photoinitiated electron collection. The collected electrons can be used to drive multi-electron processes such as the generation of hydrogen from water. They may also be used to drive the multi-electron reduction of other feedstocks, such as carbon dioxide. The supramolecular complexes are unique in that the electrons are collected on a metal center but the complex remains intact following electron collection. Interestingly, the photoreduced complexes also possess the ability to be further reduced (on the π* system of the BLs). This ability to undergo further photoreduction provides additional electrons or electrons with a higher potential available for the reduction of the substrate, i.e. water to hydrogen.

The supramolecular complexes include: one or more elements that function as light absorbers and one or more elements that function as electron acceptors or collectors. The light absorbing elements mediate charge transfer driven by the light energy that they absorb. The light absorbing elements are chemically coupled to the electron accepting elements via bridging ligands that serve as a route of transmission of the electrons from the light absorbing elements to the electron accepting elements. In addition, the light absorbing elements are typically coordinated in these complexes by terminal ligands. In some cases, the bridging ligands and the terminal ligands may be the same type of molecule.

Figure 1:
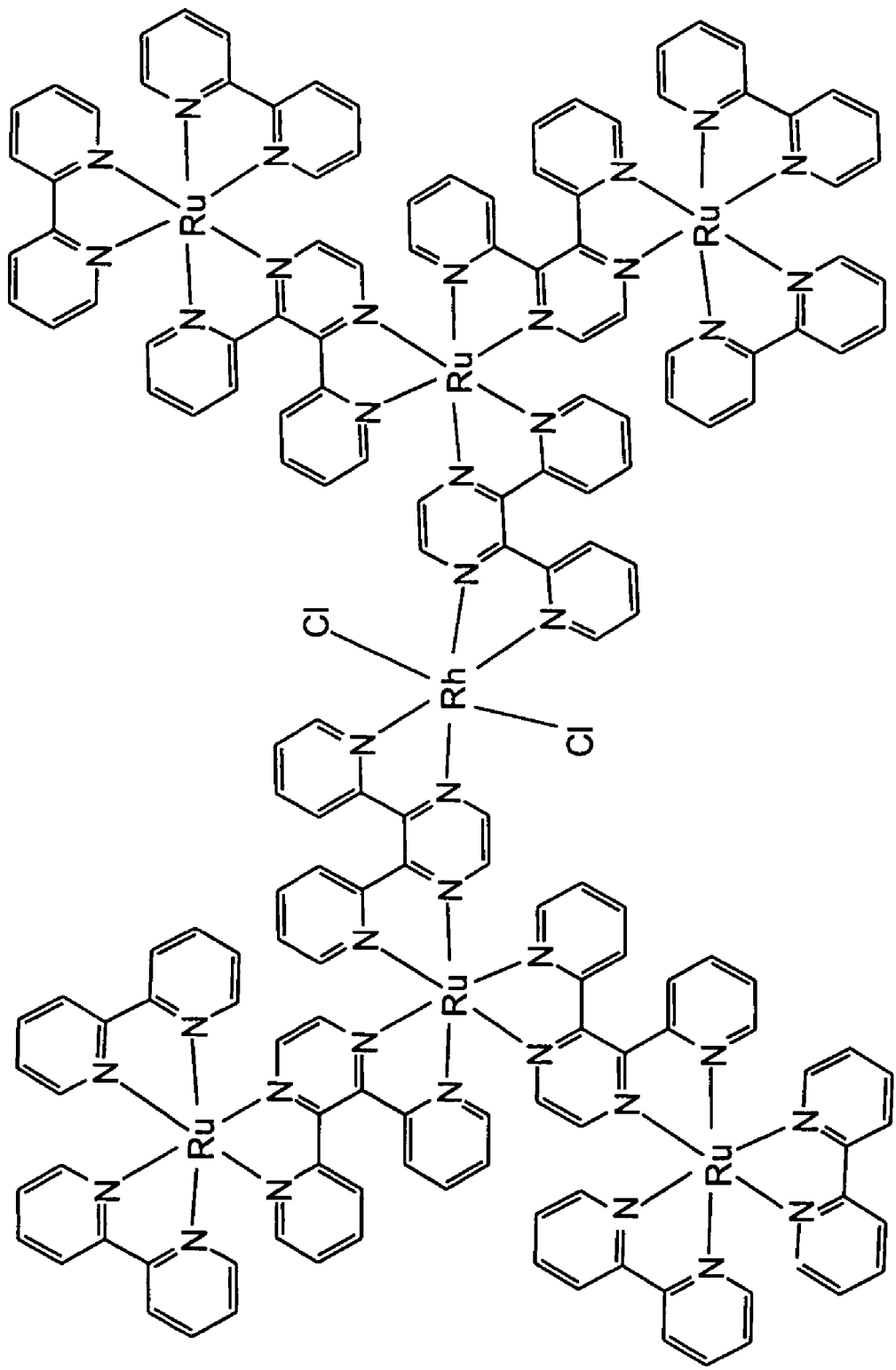
FIG. 1. Depiction of {[(bpy)$_2$Ru(dpp)]$_2$Ru(dpp)}$_2$RuCl$_2$$^{13+}$ an exemplary supramolecular complex capable of reducing water to form hydrogen.

An exemplary supramolecular complex is depicted in FIG. 1, which depicts {[(bpy)$_2$Ru(dpp)]$_2$Ru(dpp)}$_2$RhCl$_2$$^{13+}$. This complex contains six light collecting elements, each of which is Ru, and one central electron accepting element, Rh. Adjacent Ru atoms are held together by bridging 2,3'-bis(2-pyridyl)pyrazine (dpp) groups, and the central Rh is connected to two of the Ru atoms via the same molecular group. Terminal ligand 2,2'-bipyridine (bpy) groups are bonded to the four exterior Ru atoms at the outer edges of the complex.

Thus, in the supramolecular complexes, three essential components are coupled: 1) at least one metal to ligand charge transfer (MLCT) light absorbing metal center; 2) a bridging π-acceptor ligand; and 3) an electron acceptor metal center. The function of the metal to ligand charge transfer light absorber is to produce an initially optically populated metal to ligand charge transfer state. Requirements of the bridging π-acceptor ligand are that it must coordinate to both the light absorbing metal and the electron acceptor metal, and possess a π system capable of being involved in an initial metal to ligand charge transfer excitation. The requirement for the electron acceptor metal is that it bind to the bridging π-acceptor ligand and be energetically capable of accepting an electron from the optically populated MLCT state to produce a metal to metal charge transfer (MMCT) state.

The number and type of MLCT light absorbers used in the supramolecular metallic complexes of the present invention may vary, depending on several factors including but not limited to: the desired excitation wavelength to be employed; the oxidation potential of interest for the metal based highest occupied molecular orbital; the required extinction coefficient for the excitation wavelength; ease of synthesis of the complex; cost and/or availability of components; and the like. Any suitable number of MLCT light absorbers may be used so long as within the complex an initial optically populated MLCT state is produced upon exposure to light or radiant energy, which can be relayed to a suitable bridging ligand for transfer to an electron acceptor metal. In preferred embodiments, the number of MLCT light absorbers will range from 1 to about 14, and preferably from 1 to about 6, and more preferably from 1 to about 3.

Those of skill in the art will recognize that many suitable metals exist that can function as MLCT light absorbers in the practice of the present invention. Examples include but are not limited to ruthenium(II), osmium(II), rhenium (I), iron (II), platinum(II), iridium, etc. In preferred embodiments, ruthenium(II) or osmium(II) centers are utilized. Further, more than one type of light absorber may be utilized in a supramolecular complex.

The complexes of the present invention require the presence of at least one bridging π-acceptor ligand capable of being involved in an initial metal to ligand charge transfer excitation. By "bridging ligand" we mean a π-acceptor ligand that, in the supramolecular complex, is located or positioned (i.e. bonded, coordinated) between an MLCT light absorber and an electron acceptor metal. Further, if there is more than one MLCT light absorber in the complex, the bridging π-acceptor ligands will be positioned to attach each light absorbing unit to either another light absorbing unit or directly to the electron accepting metal center. The number of bridging ligands in a supramolecular complex varies depending on the number of MLCT light absorbers and electron acceptor metals in the complex. In general, the number will range from about 1 to about 14 or more.

Figure 2:
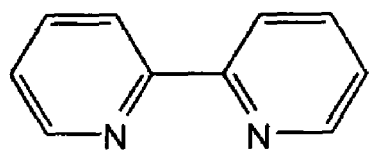
FIG. 2. Molecular structure of exemplary terminal and bridging ligands.
Figure 2:
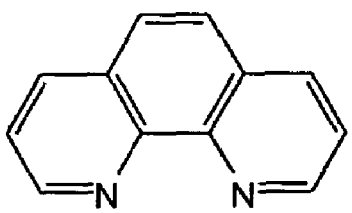
Figure 2:
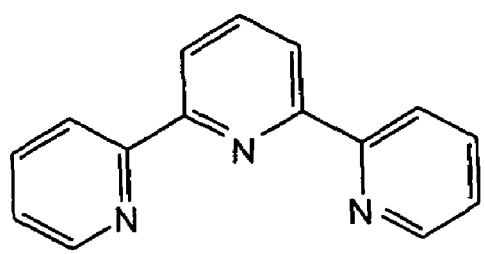
Figure 2:
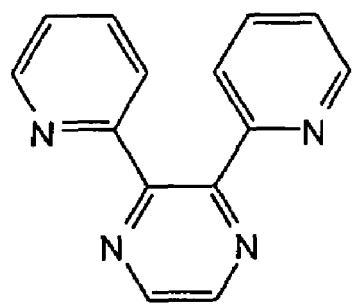
Figure 2:
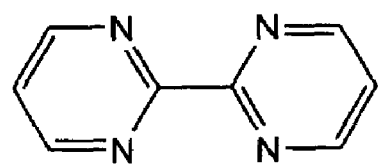

The bridging π-acceptor ligands coordinate or bind to the metal centers via donor atoms. Those of skill in the art will recognize that many suitable substances exist which contain appropriate donor atoms and may thus function as π-acceptor ligands in the complexes of the present invention. Examples include but are not limited to substances with: nitrogen donor atoms (e.g. pyridine- and pyridimidine-containing moieties such as 2,2'-bipyridine ("bpy"); 2,2':6', 2"-terpyridine ("tpy"); 2,3-bis(2-pyridyl)pyrazine ("dpp"); and 2,2'-bipyridimidine ("bpm"); 2,3-bis(2-pyridyl)quinoxaline; 2,3,5,6,-tetrakis(2-pyridyl)pyrazine; carbon and nitrogen donor atoms (e.g. 2,2'-phenylpyridine); phosphorus donor atoms (e.g. triphenylphosphine, diethylphenylphosphine); etc. In preferred embodiments of the present invention, the bridging ligands are dpp and bpm, as depicted in FIG. 2.

The supramolecular complexes of the present invention also include terminal ligands. Terminal ligands bind or coordinate to only one metal center and serve to satisfy the needed coordination sphere for the metals, thereby providing a means to tune both light absorbing and redox properties of the metal centers. Many suitable substances exist which can function as terminal ligands, many of which may also be used as bridging ligands. For example, substances with: nitrogen donor atoms (e.g. pyridine- and pyridimidine-containing moieties such as 2,2'-bipyridine ("bpy"); 2,2':6', 2"-terpyridine ("tpy"); 2,3-bis(2-pyridyl)pyrazine ("dpp"); and 2,2'-bipyridimidine ("bpm"); 2,3-bis(2-pyridyl)quinoxaline; 2,3,5,6,-tetrakis(2-pyridyl)pyrazine; carbon and nitrogen donor atoms (e.g. 2,2'-phenylpyridine); phosphorus donor atoms (e.g. triphenylphosphine, diethylphenylphosphine); etc. In preferred embodiments of the present invention, the terminal ligands are bpy, phen, and tpy, as depicted in FIG. 2. In a supramolecular complex, the bridging and terminal ligands may be the same type of molecule but fulfill a different function in the complex according to location, or the bridging and terminal ligands may be different molecules. In addition, two or more different types of molecules may function as terminal ligands in a supramolecular complex.

Further, those of skill in the art will recognize that, depending on the number of available coordination sites on the metals to which the π-acceptor ligands are coordinated, other extraneous ligands (e.g. counterions) may also be present to complete the coordination sphere of the metal. Examples of such ligands include but are not limited to suitable forms (e.g. ionized, if appropriate) of: halogens such as Cl and Br, COOH, CO, $H_2O$, $CH_3CN$, $PF_6$, phosphines, pyridines, hydrides, etc.

The electron acceptor metal is an essential component of this molecular design. Those of skill in the art will recognize that many metals may be used as the electron acceptor metal in the complexes of the present invention. Examples of suitable metals include but are not limited to rhodium(III), platinum(IV), cobalt(III), iridium(III). Any metal that can bind to a bridging π-acceptor ligand and accept an electron from the optically populated MLCT state to produce the reactive MMCT state may be utilized. In a preferred embodiment of the invention, the electron acceptor metal is rhodium(III). Further, the number of electron acceptor metal centers in the complex may also be varied. Multifunctional systems could be designed that use many electron acceptor sites to enhance the functioning of the system by providing additional active sites within a single molecular architecture. Importantly, the design of the supramolecular complexes of the present invention is such that the complex remains intact and is not destroyed upon carrying out catalytic functions (e.g. the reduction of water to produce hydrogen). The advantage of this attribute is that systems employing the supramolecular complexes of the present invention are capable of carrying out repeated catalytic reactions when coupled to electron donors or water oxidation and are thus long-lived in comparison to prior art systems. The light absorbers remaining attached to the electron acceptor following electron collection allow the complexes to undergo further charge transfer excitation, leading to subsequent reduction of the complexes.

In general, the supramolecular architecture of the complexes of the present invention can be varied by changing the identity and number of components of the complex. However, it is necessary to retain the components in sufficiently close association and appropriate orientation to provide the necessary electronic coupling. This coupling is necessary to allow electron transfer from the initial π-acceptor ligand (that accepts the charge in the initially populated metal to ligand charge transfer state) to the electron accepting metal center. Those of skill in the art will recognize that the precise distances between components and the orientation of the components will vary from complex to complex, depending on the identity of complex substituents. However, in general the distances will be confined to the multi-atomic or multi-angstrom scale.

Exemplary forms of the complexes of the invention contain two ruthenium- or osmium-based light absorbers which are coupled to a reactive rhodium metal site. In these embodiments, the light absorbing metal centers are occupied by Ru or Os, and the central electron acceptor metal site is occupied by Rh.

Preferred embodiments of the complexes include:
[(bpy)$_2$Ru(dpp)RhCl$_2$(dpp)Ru(bpy)$_2$](X)$_5$
[(bpy)$_2$Os(dpp)RhCl$_2$(dpp)Os(bpy)$_2$](X)$_5$
[(tpy)RuCl(bpm)RhCl$_2$(bpm)RuCl(tpy)](X)$_3$ and
[(tpy)RuCl(dpp)RhCl$_2$(dpp)RuCl(tpy)](X)$_3$;

where X is a counterion such as $PF_6^-$, $Cl^-$, $Br^-$, $CF_3SO_3^-$, $BF_4^-$, $ClO_4^-$, $SO_4^{2-}$, etc. Those of skill in the art will recognize that many such suitable counterions exist and may be utilized to form the salt form of a complex without altering the fundamental properties of the complex, other than its solubility.

Synthesis of the supramolecular complexes of the present invention can be carried out by a building block approach. Typically using this method the terminal metals on the outside of the complex are prepared first, reacting them with the desired terminal ligands, i.e. bpy, tpy, etc. Once the terminal metal is coordinated to the terminal ligand, reaction with a bridging ligand assembles that sub-unit of the supramolecular complexes. These synthons are then reacted with additional metals, either secondary light absorbing units or the reactive metal. This means of assembly allows for control of supramolecular structure. Alternatively the complexes can be assembled from the center out by reacting the desired bridging ligands with the reactive metal followed by coupling to the light absorbing units.

Suitable wavelengths of light for use in the practice of the present invention are dependent on the components of a given supramolecular complex. In general, visible and ultraviolet light can be utilized. By "visible light" we mean light of wavelengths greater than about 400 nm. In general, the wavelength used will depend on the complex of interest and its ability to absorb at that wavelength. Typically excitation would occur in the region of the intense metal to ligand charge transfer excitation. For example, for the system $[\{(bpy)_2Ru(dpp)\}_2RhCl_2](PF_6)_5$ the lowest lying MLCT transition center is at 514 nm so optimal excitation would occur in this region (±about 50 nm) i.e. from about 464 to about 564 nm. However, those of skill in the art will recognize that other excitations further from the optimum can also be used due to the efficient internal conversion within supramolecular complexes of the type described herein. For example, for an exemplary system such as $[\{(bpy)_2Ru(dpp)\}_2RhCl_2](PF_6)_5$ excitation is possible throughout the UV and into the visible region, i.e. from about 200 to about 650 nm. Suitable sources of excitation include various well-known artificial sources and natural sunlight.

Figure 3:
FIG. 3. Schematic representation of an exemplary method of the invention.

The invention also provides a method of producing hydrogen from water. The method is illustrated in FIG. 3. As is illustrated, the method involves exposing the water to a supramolecular complex of the invention and to radiant energy. While the FIG. 3 illustrates exposure as two steps, those of skill in the art will recognize that in order for $H_2$ generation to occur, the water can be exposed to both the complex and the radiant energy at the same time.

The invention further provides a system/apparatus for catalyzing the reduction of water to form hydrogen which incorporates these materials either photochemically or electrochemically. Amouyal and Sauvage have highlighted systems that photochemically produce hydrogen from water in separate reviews. ("Photochemical production of hydrogen and oxygen from water: A review and state of the art," Edmond Amouyal *Solar Energy Materials and Solar Cells* 1995, 38, 249. "Hydrogen Generation by Visible Light Irradiation of Aqueous Solutions of Metal Complexes. An approach to the Photochemical Conversion and Storage of Solar Energy," Michele Kirch, Jean-Marie Lehn, Jean-Pierre Sauvage, *Helv. Chim. Acta* 1979, 62, 1345. A system to produce hydrogen from water using light would include the supramolecular complexes as described herein and additional components that would be involved in the electron donation and the use of the oxidizing equivalents to oxidize a substrate, for example the oxidation of water to oxygen. The general design of such systems is known to those of skill in the art, and can readily be adapted to include the present supramolecular complexes. The supramolecular complexes will perform the function of light absorber, electron collector and catalyst for the conversion of light energy into chemical energy. The supramolecular complexes could be in solution or attached to a support, depending on whether homogeneous or heterogeneous catalysis is desired.

In a preferred embodiment of the invention, the system is coupled to a water oxidation cycle that produces oxygen and allows water to function as the electron donor. However, those of skill in the art will recognize that other electron donors may also be used in the methods of the present invention, including but not limited to dimethylaniline (DMA), triethanolamine (TEOA), triethylamine (TEA), ascorbic acid, etc.

Figure 4:
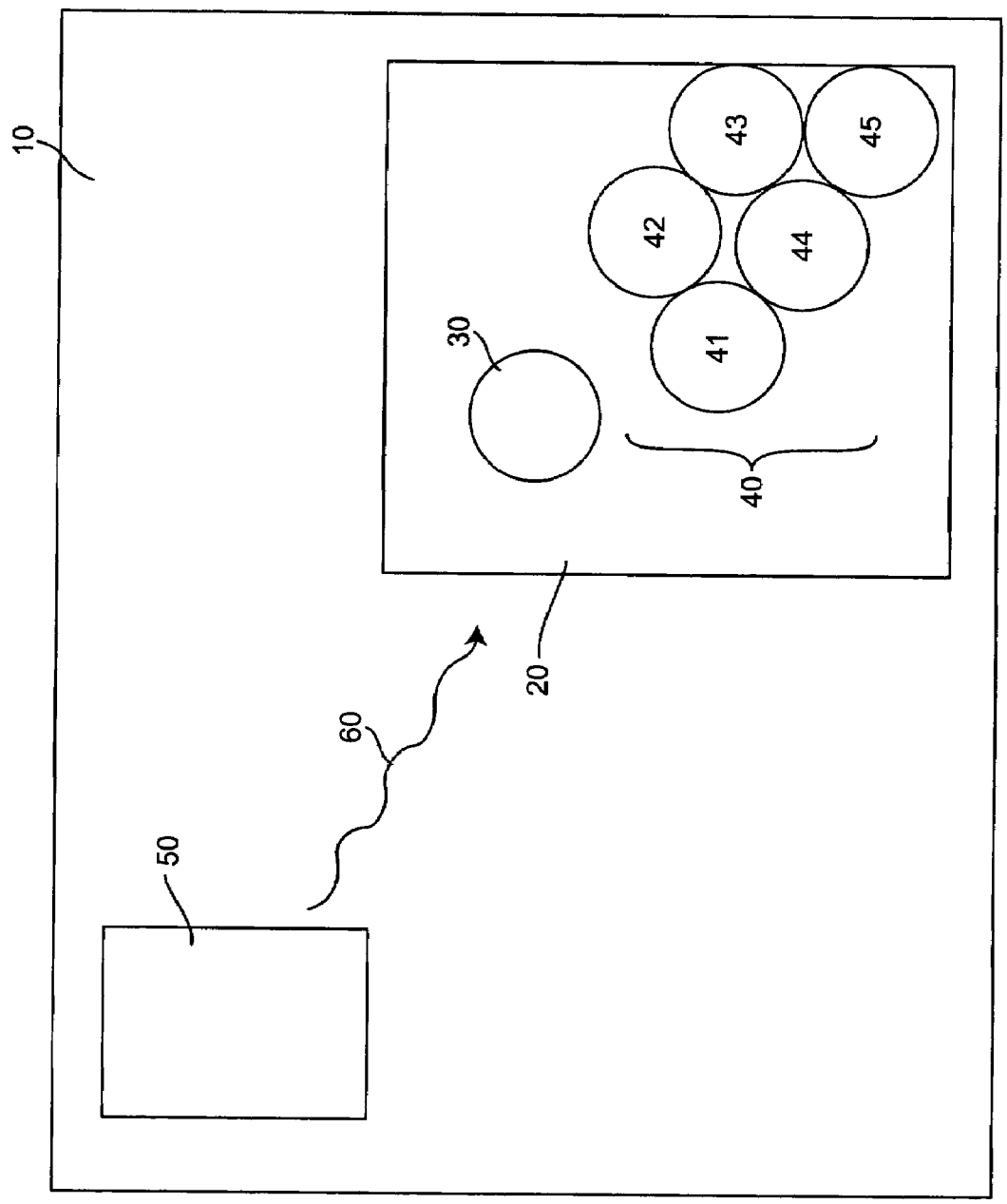
FIG. 4. Schematic representation of the system of the present invention.

FIG. 4 illustrates an exemplary system for reducing water to produce hydrogen. As illustrated in the Figure, the system 10 comprises a vessel 20 for containing water 30 and a supramolecular complex 40. The supramolecular complex 40 comprises at least one metal to ligand charge transfer light absorbing metal 41, at least one bridging π-acceptor ligand 42; at least one electron acceptor metal 43; at least one terminal ligand 44; and an electron donor 45 which interacts with the supramolecular complex. The system further comprises means 50 for directing radiant energy 60 towards the vessel.

The system of the present invention may be considered as one half of a solar water splitting scheme, the fuel production side. For this to function in a light to energy conversion scheme, the system is coupled to oxidation such as water to oxygen or another system that uses oxidizing equivalents. This is typically done by oxidizing water to oxygen. In one system used to demonstrate the present invention, a sacrificial electron donor is utilized. The donor can then be used as an oxidizing equivalent relay to couple to a complementary oxidation process. The oxidation chemistry is typically not photochemical but rather simple redox chemistry. For example, in a solar cell that uses light energy to split water, the light energy excites electrons at a collection site that then reacts with water to produce hydrogen. The oxidizing equivalents move to the positive electrode and are collected at a catalyst that can oxidize water to oxygen to complete a catalytic cycle.

The following examples are to be considered as exemplary of various aspects of the present invention and are not intended to be limiting with respect to the practice of the invention. Those of ordinary skill in the art will appreciate that alternative materials, conditions, and procedures may be varied and remain within the skill of the ordinarily skilled artisan without departing from the general scope of the invention as taught in the specification.

EXAMPLES

Example 1

Synthesis of Ruthenium Light Absorbers Coupled to Rhodium

Figure 5A:
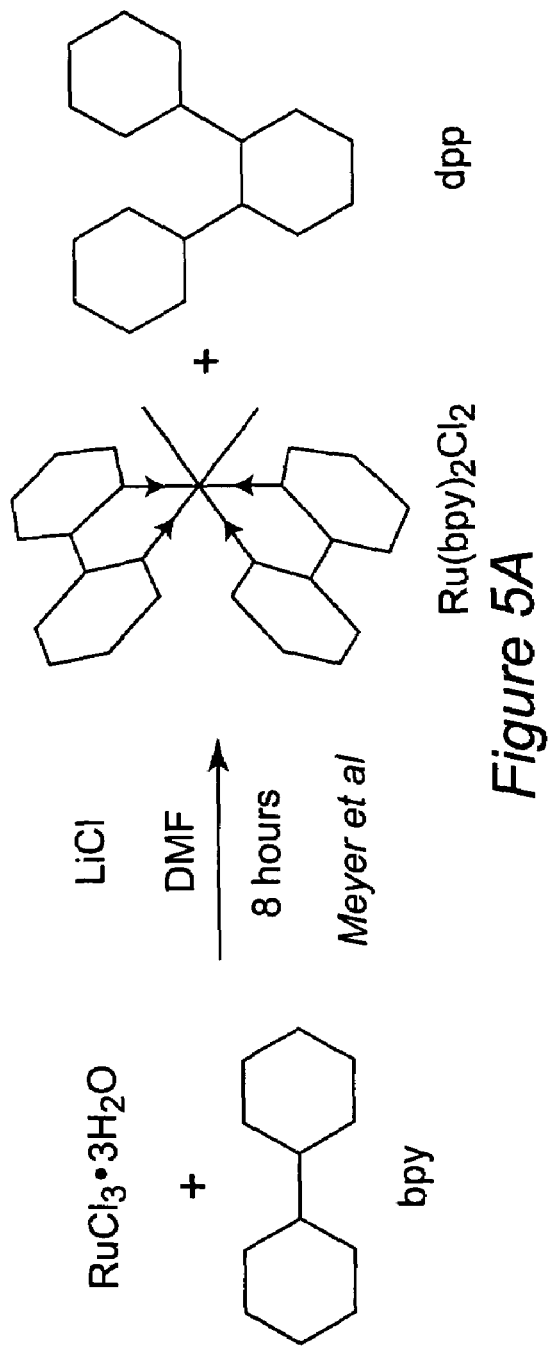
FIG. 5A–D. Exemplary synthesis scheme. A, synthesis of Ru(bpy)$_2$Cl$_2$ and dpp; B, synthesis of [(bpy)$_2$Ru(dpp)]$^{2+}$; C, synthesis of [(bpy)$_2$Ru(dpp)RhCl$_2$(dpp)Ru(bpy)$_2$]$^{5+}$; D, illustration of charge transfer in [(bpy)$_2$Ru(dpp)RhCl$_2$(dpp)Ru(bpy)$_2$]$^{5+}$.
Figure 5B:
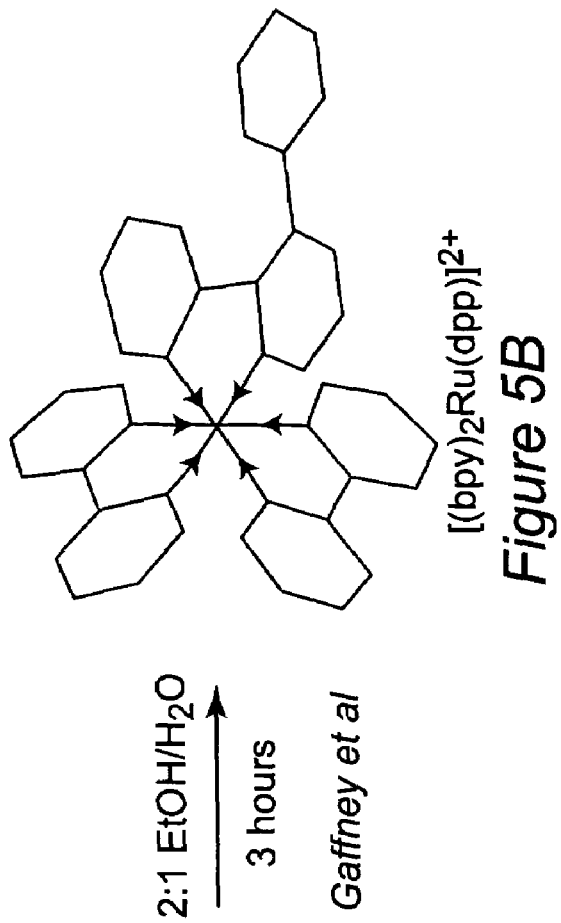

The supramolecular complex $[(bpy)_2Ru(dpp)RhCl_2(dpp)Ru(bpy)_2]^{5+}$ was synthesized as follows: 1) the ruthenium light absorber $[(bpy)_2Ru(dpp)]^{2+}$ was synthesized as illustrated in FIGS. 5A and B.

Figure 5C:
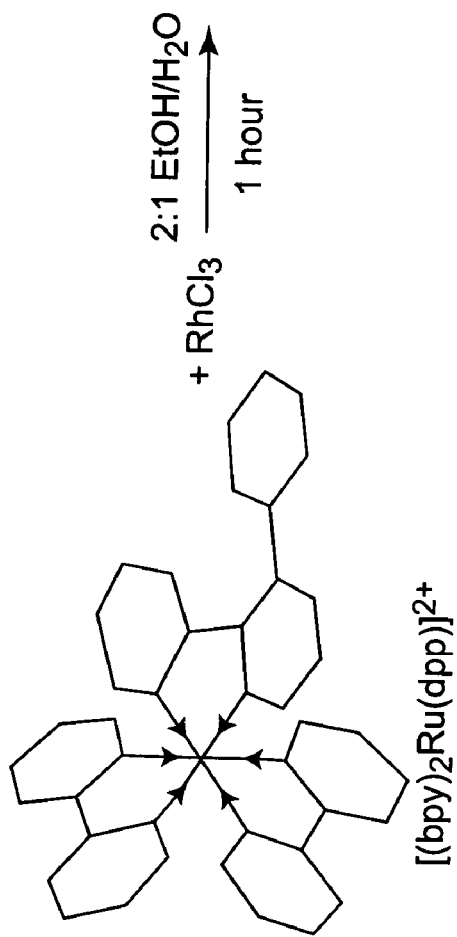
Figure 5D:
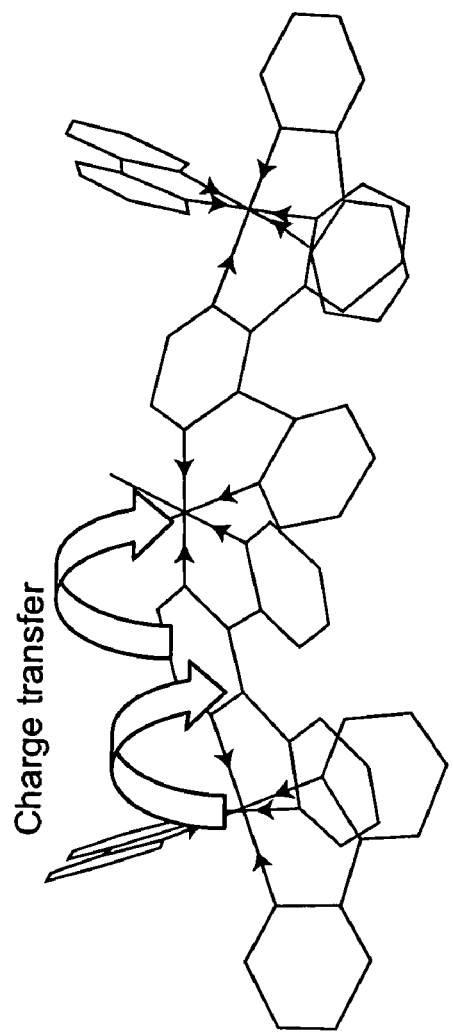
Figure 6A:
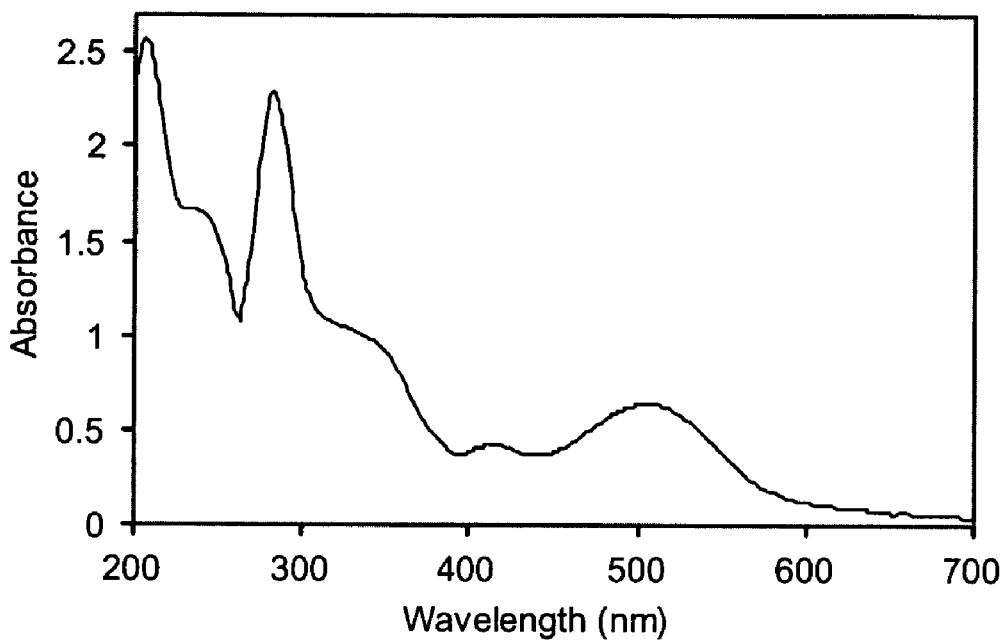
FIGS. 6A and B. A, absorbance profile of [(bpy)$_2$Ru(dpp)RhCl$_2$(dpp)Ru(bpy)$_2$]$^{5+}$; B, schematic illustration of the excitation mechanism of [(bpy)$_2$Ru(dpp)RhCl$_2$(dpp)Ru(bpy)$_2$]$^{5+}$. $^1$GS=ground state; $^1$MLCT=singlet metal to ligand charge transfer; $^3$MLCT=triplet metal to ligand charge transfer; $^3$MMCT=triplet metal to metal charge transfer; $k_{isc}$=rate of intersystem crossing; $k_r$=rate of radiative decay; $k_{nr}$=rate of non-radiative decay; $k_{et}$=rate of electron transfer.
Figure 6B:
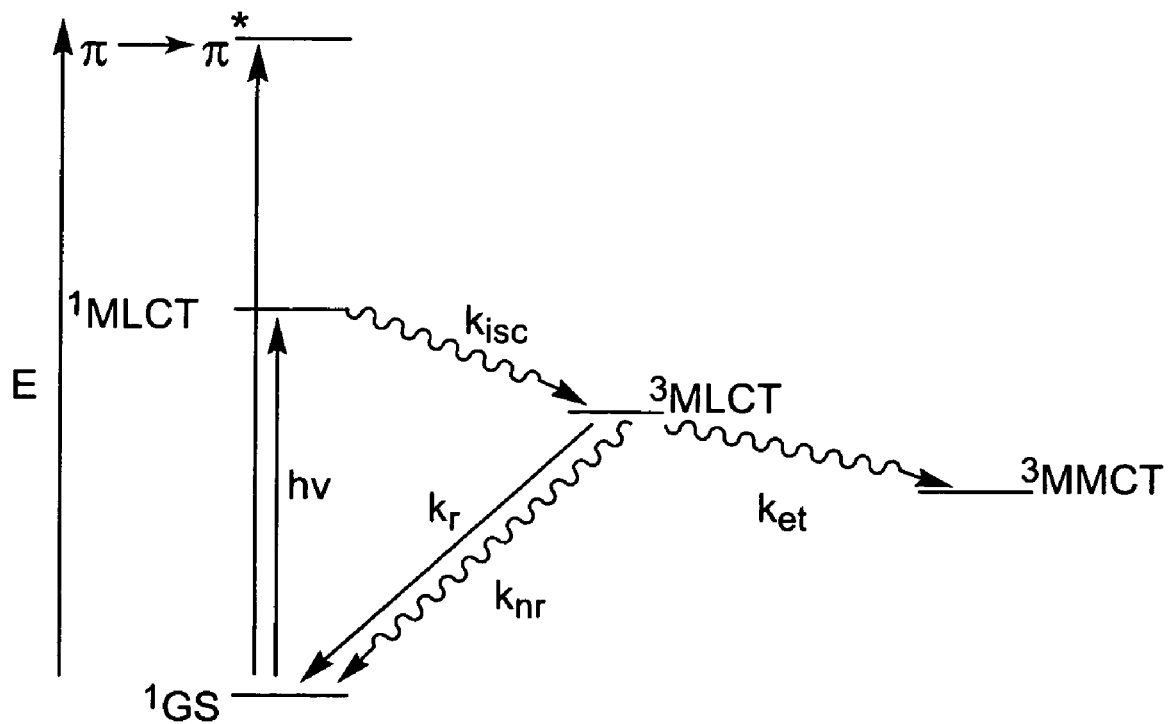

Synthesis of the supramolecular complexes of the present invention can be carried out by a building block approach. Typically using this method the terminal metals on the outside of the complex are prepared first, reacting them with the desired terminal ligands, i.e. bpy, tpy, etc. For this example the bpy ligand is bound to the Ru to produce $[Ru(bpy)_2Cl_2]$. Once the terminal metal is coordinated to the terminal ligand, reaction with a bridging ligand assembles that sub-unit of the supramolecular complexes. This would involve the reaction of the bridging ligand dpp to produce $[(bpy)_2Ru(dpp)]^{2+}$ for this example. These synthons are then reacted with additional metals, either secondary light absorbing units or the reactive metal. This would involve the reaction of the $[(bpy)_2Ru(dpp)]^{2+}$ with $RhCl_3^-xH_2O$ to produce the supramolecular complex, [(bpy)$_2$Ru(dpp)RhCl$_2$(dpp)Ru(bpy)$_2$]$^{5+}$. These means of assembly allows for control of supramolecular structure. Alternatively the complexes can be assembled from the center out by reacting the desired bridging ligands with the reactive metal followed by coupling to the light absorbing units. The coupling of [(bpy)$_2$Ru(dpp)]$^{2+}$ to rhodium is illustrated in FIG. 5C. As can be seen, the resulting mixed-metal supramolecular complex is [(bpy)$_2$Ru(dpp)RhCl$_2$(dpp)Ru(bpy)$_2$]$^{5+}$. Two charge transfer pathways within the complex are indicated by arrows (5D). FIG. 6A shows the absorbance profile of [(bpy)$_2$Ru(dpp)RhCl$_2$(dpp)Ru(bpy)$_2$]$^{5+}$ and FIG. 6B shows the general excitation mechanism for such supramolecular complexes. As can be seen, excitation is typically through the intense metal to ligand charge transfer transition. This excitation is then followed by intersystem crossing to produce the triplet excited state. This is followed by intramolecular electron transfer to produce the triplet metal to metal charge transfer. A variety of other excitation pathways are possible and either the metal to ligand or metal to metal charge transfer state can be responsible for the desired photochemical reduction of the supramolecular complex.

Example 2

Electrochemistry of [(bpy)$_2$Ru(dpp)RhCl$_2$(dpp)Ru(bpy)$_2$](PF$_6$)$_5$

Figure 7A:
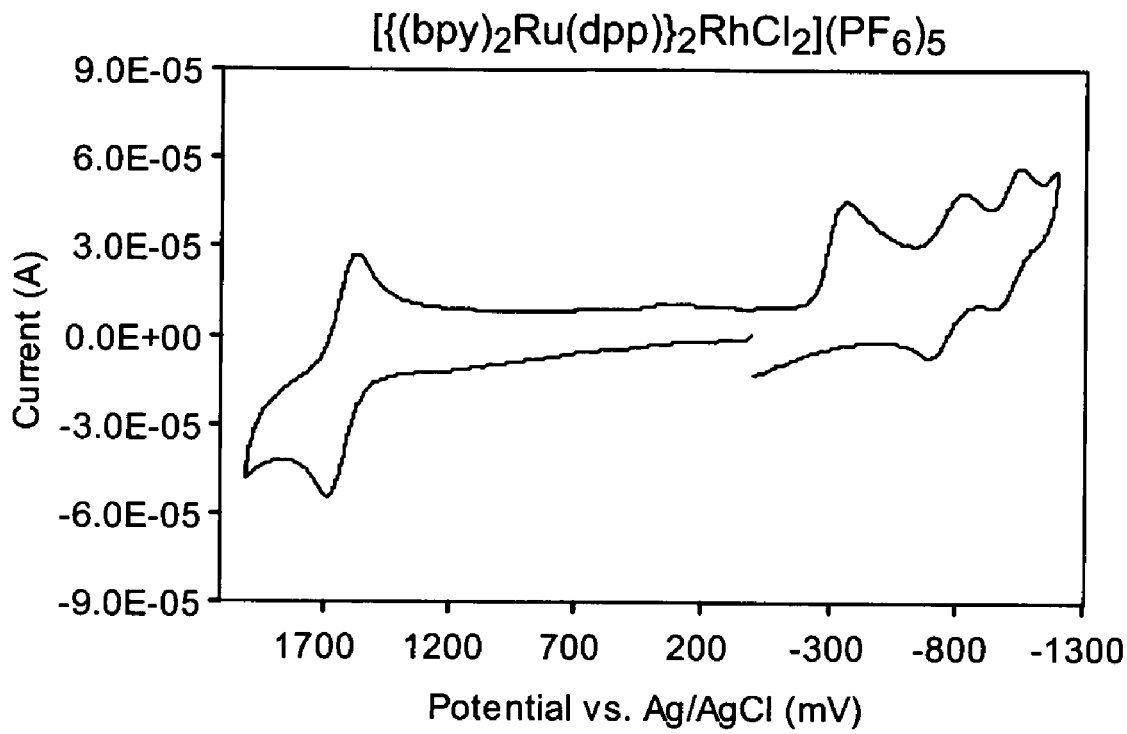
FIG. 7. Cyclic voltammetry of [(bpy)$_2$Ru(dpp)RhCl$_2$(dpp)Ru(bpy)$_2$](PF$_6$)$_5$. A, and B. Orbital energy diagram for [(bpy)$_2$Ru(dpp)RhCl$_2$(dpp)Ru(bpy)$_2$](PF$_6$)$_5$.
Figure 7B:
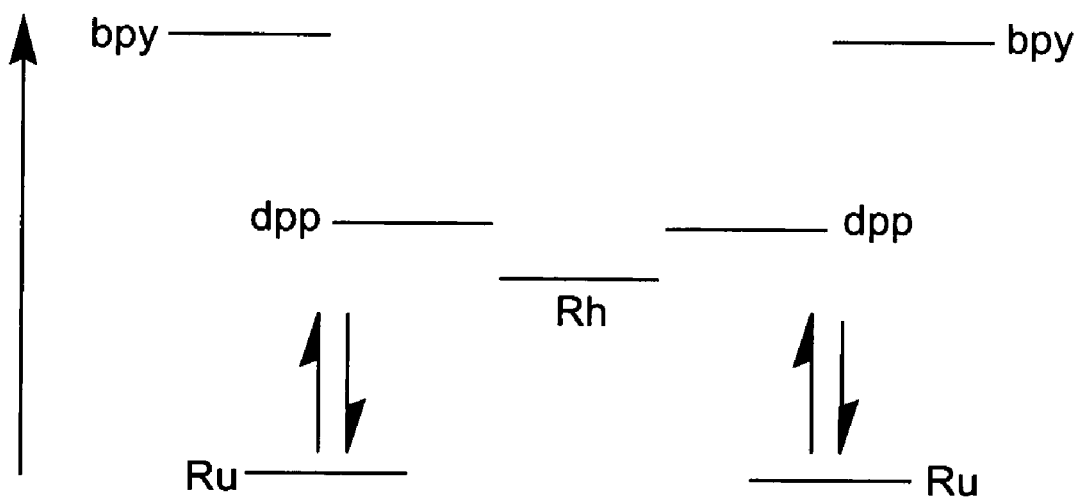

Cyclic voltammetry: FIGS. 7A and B illustrate the electrochemical properties of the [(bpy)$_2$Ru(dpp)RhCl$_2$(dpp)Ru(bpy)$_2$](PF$_6$)$_5$ complex. The data show the Ru nature of the highest occupied molecular orbital and the Rh nature of the lowest unoccupied molecular orbital on the supramolecular complex. This data also provides the energy of the frontier orbitals in this complex, which relate to the reducing power of the reduced form of the complexes and to the energy of the optically populated states.

Figure 8:
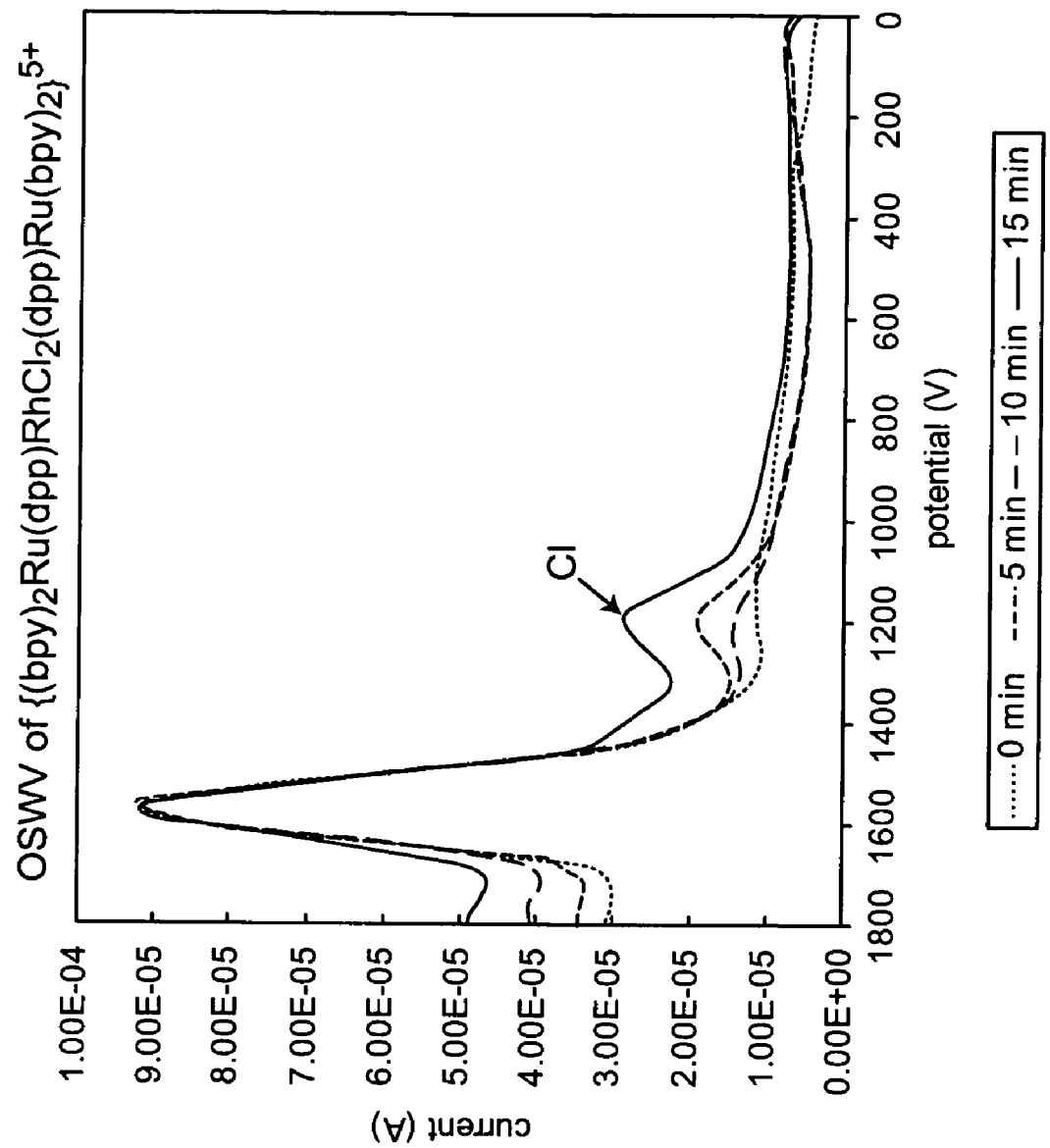
FIG. 8. Bulk Electrolysis of [(bpy)$_2$Ru(dpp)RhCl$_2$(dpp)Ru(bpy)$_2$](PF$_6$)$_5$. OSWV=Osteryoung square wave voltammogram.

Bulk Electrolysis: FIG. 8 illustrates the electrochemical properties of the reduced form of the [(bpy)$_2$Ru(dpp)RhCl$_2$(dpp)Ru(bpy)$_2$](PF$_6$)$_5$ complex. The data show the Rh nature of the lowest unoccupied molecular orbital as well as the reactivity of the electrochemically generated Rh(I) state. In addition, the data show the production of free chloride upon reduction of the supramolecular complex.

Figure 9:
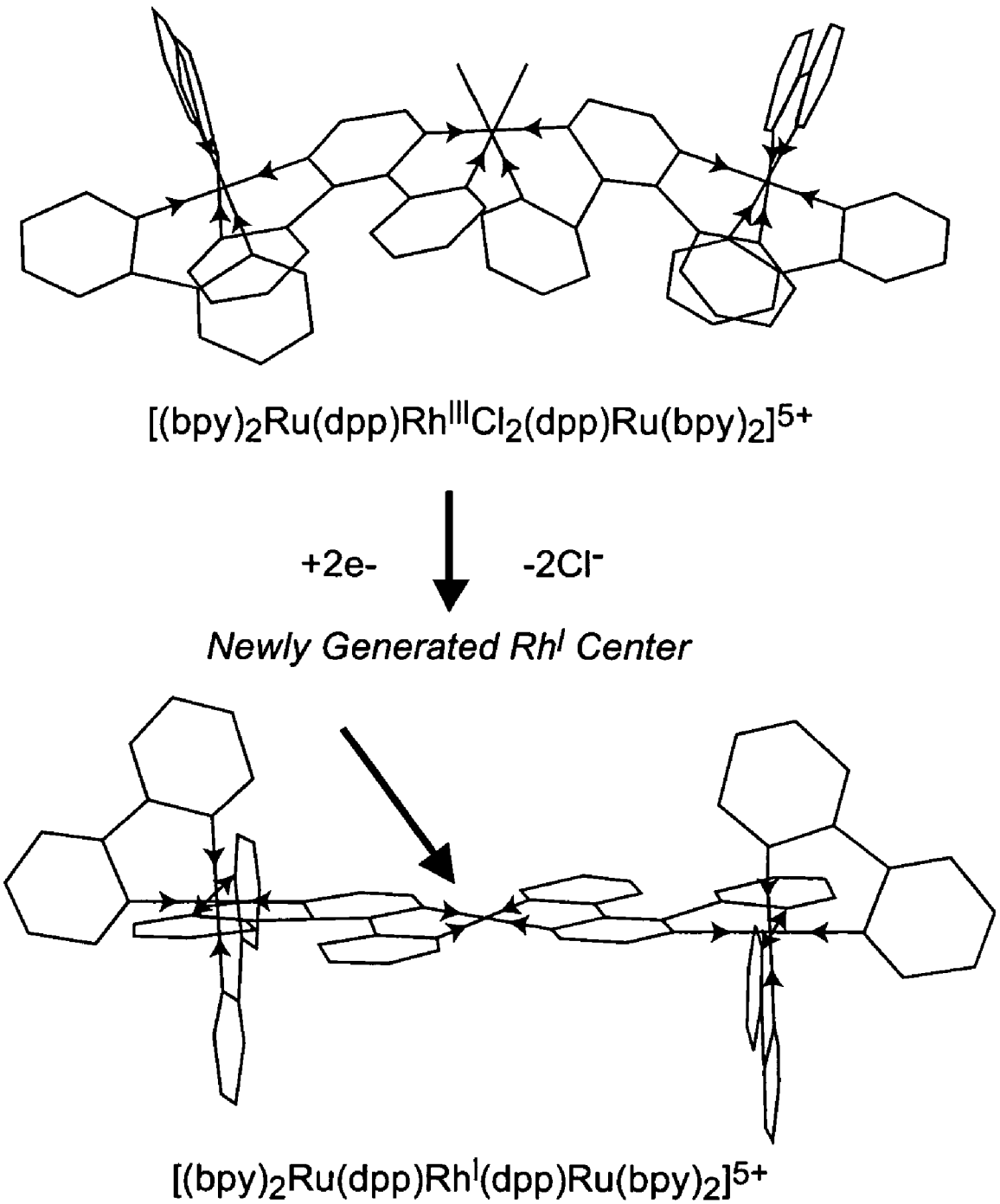
FIG. 9. Steric alterations of Rh metal center of [(bpy)$_2$Ru(dpp)RhCl$_2$(dpp)Ru(bpy)$_2$](PF$_6$)$_5$ resulting from reduction.

FIG. 9 shows the steric alterations that the Rh metal center undergoes as a result of the collection of two electrons by the Rh metal center. During the reaction, Rh$^{III}$ is reduced to Rh$^{I}$. The reduced form of Rh prefers to be square planar and does so by loss of two chloride ligands as well as via stereochemical rearrangement.

Example 3

Figure 10A:
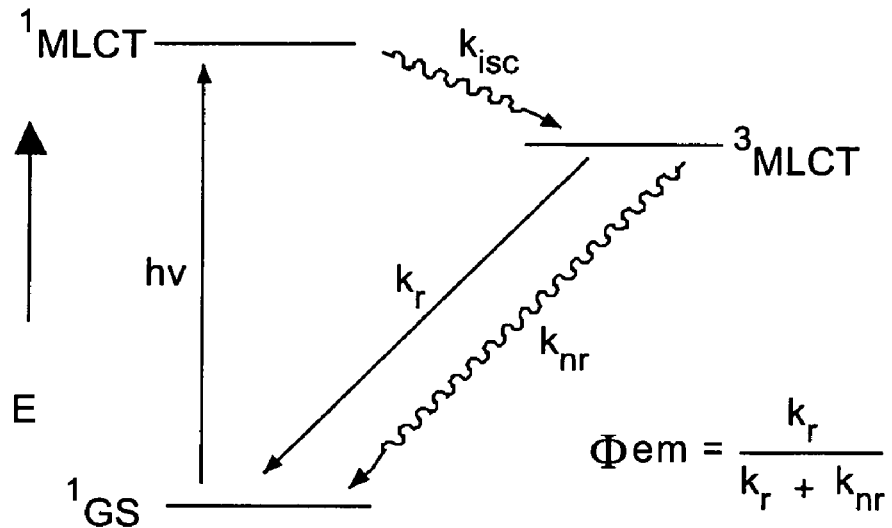
FIGS. 10A and B. Excitation mechanism of A, [(bpy)$_2$Ru(dpp)Ru(bpy)$_2$]$^{4+}$ and B, [(bpy)$_2$Ru(dpp)RhCl$_2$(dpp)Ru(bPy)$_2$]$^{5+}$.
Figure 10B:
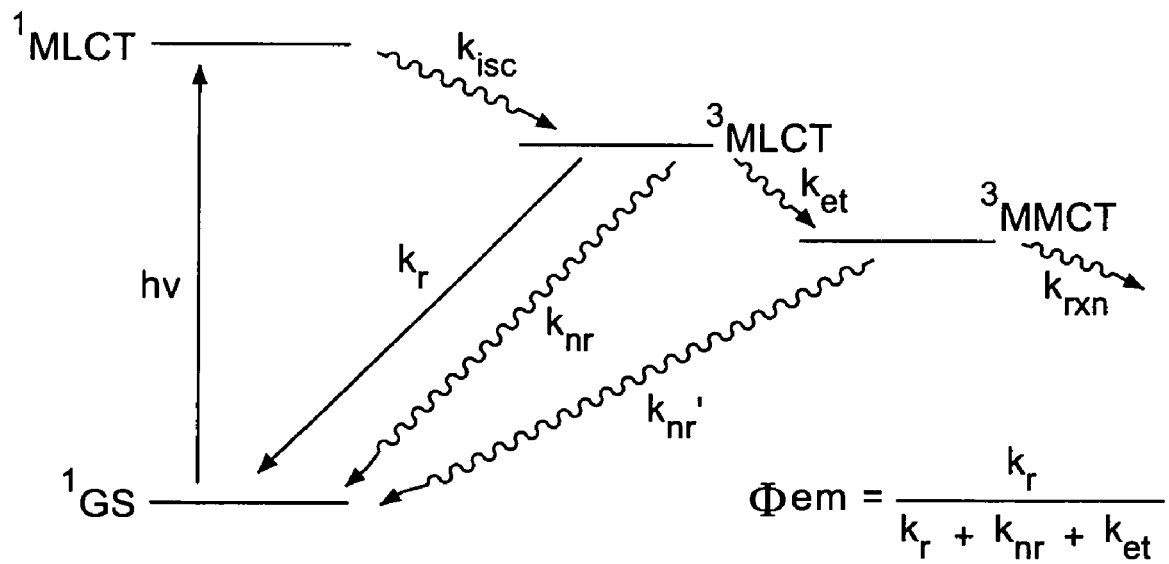
Figure 11:
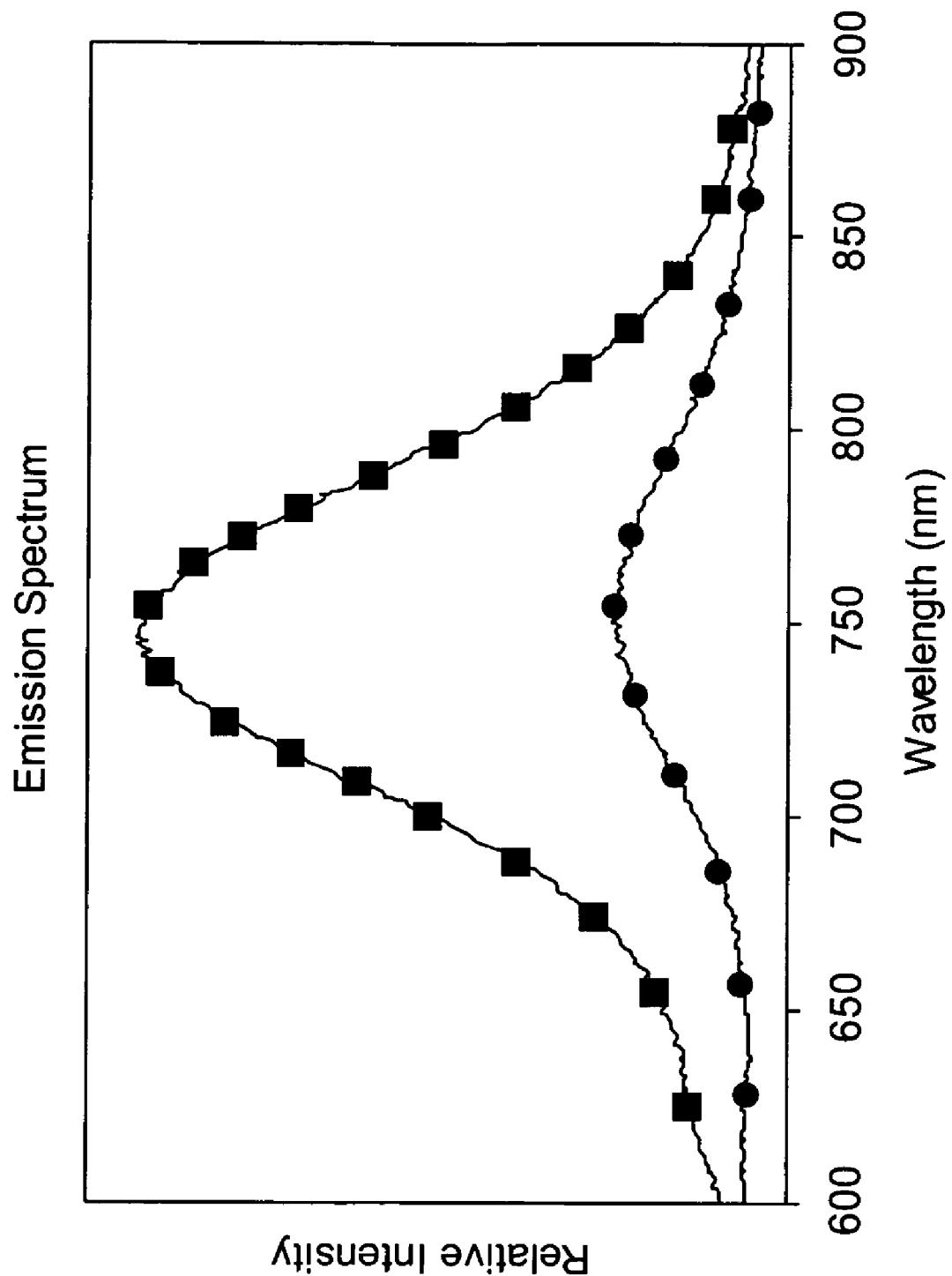
FIG. 11. Emission spectra of [(bpy)$_2$Ru(dpp)Ru(bpy)$_2$]$^{4+}$ (●) and [(bpy)$_2$Ru(dpp)RhCl$_2$(dpp)Ru(bpy)$_2$](PF$_6$)$_5$ (■).

A Comparison of Photophysical Properties of [(bpy)$_2$Ru(dpp)Ru(bpy)$_2$]$^{4+}$ and [(bpy)$_2$Ru(dpp)RhCl$_2$(dpp)Ru(bpy)$_2$]$^{5+}$ FIGS. 10A and B illustrate the excitation mechanism of [(bpy)$_2$Ru(dpp)Ru(bpy)$_2$]$^{4+}$ and [(bpy)$_2$Ru(dpp)RhCl$_2$(dpp)Ru(bpy)$_2$]$^{5+}$, respectively. This illustrates the presence of the low lying MMCT state in the Rh containing complex, consistent with the Rh based lowest unoccupied molecular orbital. FIG. 11 depicts the emission spectra of [(bpy)$_2$Ru(dpp)Ru(bpy)$_2$]$^{4+}$ and [(bpy)$_2$Ru(dpp)RhCl$_2$(dpp)Ru(bpy)$_2$](PF$_6$)$_5$. As can be seen, the emission from the Rh complex is significantly quenched relative to the Ru only complex, indicative of efficient electron transfer from the metal to ligand charge transfer state to produce the metal to metal charge transfer state.

The excited state lifetime ($\tau$) of [(bpy)$_2$Ru(dpp)Ru(bpy)$_2$]$^{4+}$ ("Electrochemical, Spectroscopic and Spectroelectrochemical Properties of Synthetically Useful Supramolecular Light Absorbers with Mixed Polyazine Ligands," Brauns, E.; Jones, S. W.; Clark, J. A.; Molnar, S. M.; Kawanishi, Y.; Brewer, K. J. *Inorg. Chem.* 1997, 36, 2861–2867) and [(bpy)$_2$Ru(dpp)RhCl$_2$(dpp)Ru(bpy)$_2$]$^{5+}$ were measured and compared. For these calculations, $\tau=1/k$ and y=a+b [exp(-kt)]. The results with both compounds showed that the value of $\tau$ for [(bpy)$_2$Ru(dpp)Ru(bpy)$_2$]$^{4+}$ is 153±5 nanoseconds and that of [(bpy)$_2$Ru(dpp)RhCl$_2$(dpp)Ru(bpy)$_2$]$^{5+}$ is 45±5 nanoseconds.

Table 1 summarizes the photophysical properties of the two compounds.

TABLE 1

| Complex | [(bpy)$_2$Ru(dpp)RhCl$_2$(dpp)Ru(bpy)$_2$]$^{5+}$ | [(bpy)$_2$Ru(dpp)Ru(bpy)$_2$]$^{4+}$ |
|---|---|---|
| $\lambda_{max}^{abs}$ (nm) | 515 | 520 |
| $\lambda_{max}^{em}$ (nm) | 750 | 750 |
| $\Phi^{em}$ | $7 \times 10^{-4}$ | $3 \times 10^{-3}$ |
| $\tau$ (ns) | 45 | 153 |

Further, with respect to the excitation mechanisms illustrated in FIG. 11, $k_{et}=2.6\times10^7 s^{-1}$ and $k_{et}=1.6\times10^7 s^{-1}$ calculated using quantum yield for emission and lifetimes, respectively. This data shows that intramolecular electron transfer is rapid and therefore population of the metal to metal charge transfer state is expected to be efficient.

Example 4

Electron Collection by [(bpy)$_2$Ru(dpp)RhCl$_2$(dpp)Ru(bpy)$_2$](PF$_6$)$_5$

Figure 12A:
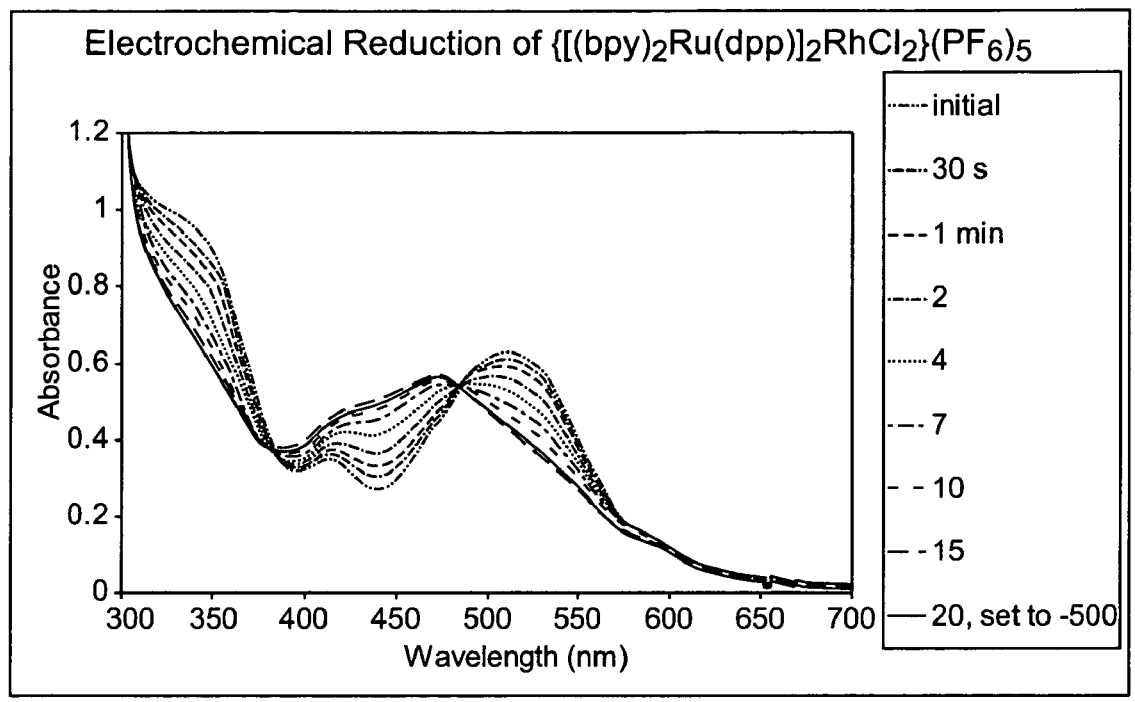
FIG. 12A and B. A, electrochemical and B, photochemical reduction of [{(bpy)$_2$Ru(dpp)}$_2$RhCl$_2$](PF$_6$)$_5$.
Figure 12B:
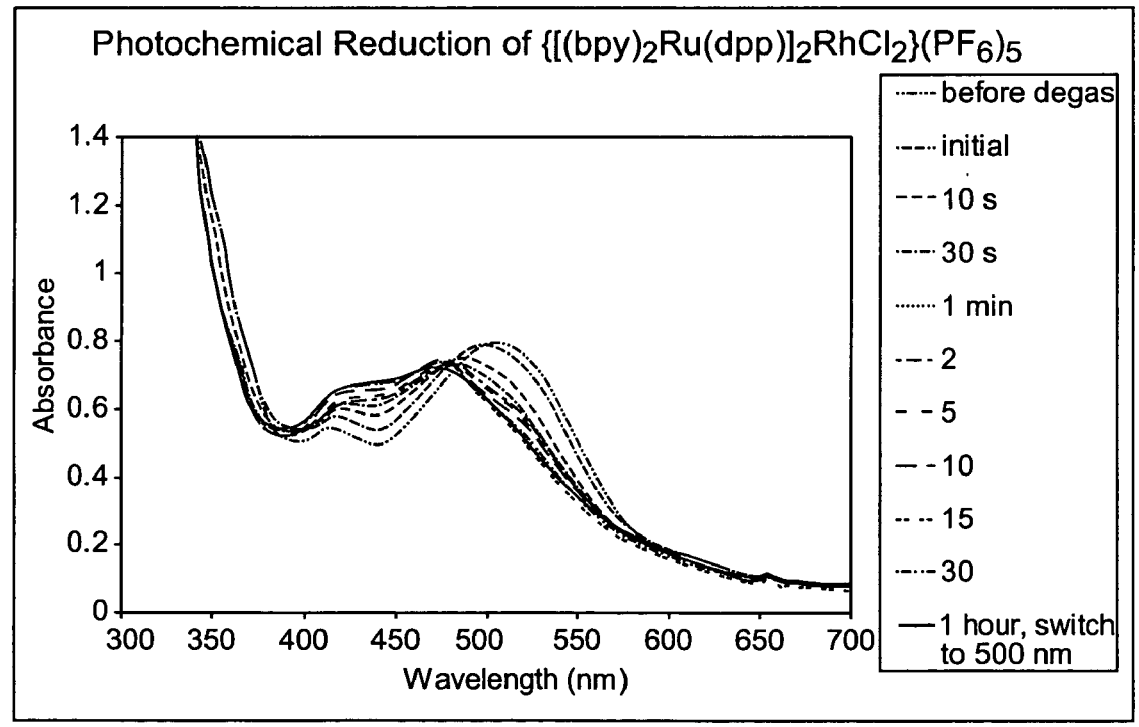

The absorbance profiles of [(bpy)$_2$Ru(dpp)RhCl$_2$(dpp)Ru(bpy)$_2$](PF$_6$)$_5$ during photoinitiated electron collection were recorded and are depicted in FIGS. 12A and B. FIGS. 12A and B show the results of electrochemical and photochemical reduction of [(bpy)$_2$Ru(dpp)RhCl$_2$(dpp)Ru(bpy)$_2$](PF$_6$)$_5$, respectively. As can be seen, it is possible to photochemically produce the two electron reduced form of the complex, Rh(I). Further photoreduction is also possible to yield the four electron reduced form in which both dpp ligands are also reduced.

Example 5

Hydrogen generation by $[(bpy)_2Ru(dpp)RhCl_2(dpp)Ru(bpy)_2]^{5+}$

Figure 13:
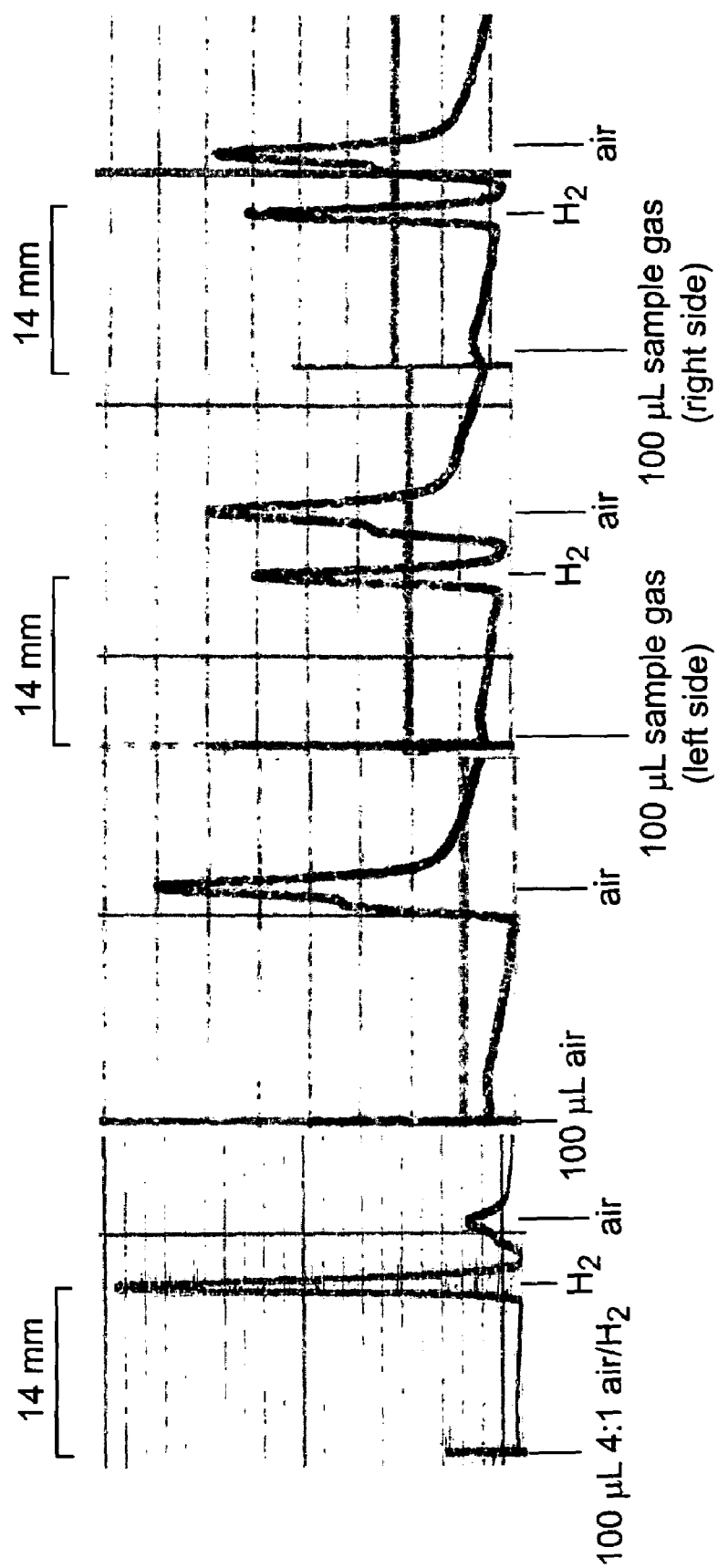
FIG. 13. Gas chromatograms showing photoinitiated production of hydrogen.

The ability of $[(bpy)_2Ru(dpp)RhCl_2(dpp)Ru(bpy)_2]^{5+}$ to generate hydrogen from water was tested. The experiment was carried out as follows: the complex was dissolved in $CH_3CN/H_2O$ mixture, dimethylaniline added, and the solution photolyzed with 500±0.25 nm light. Other wavelengths of light are also effective so long as they overlap with an absorbance of the complex. The system was photolyzed for a variety of times from ca. 30 minutes to 4 hours. Hydrogen was detected using gas chromatography with an Ar carrier gas and a molecular sieve column. The results that were obtained are presented in FIG. 13. As can be seen significant amounts of hydrogen are produced upon photolysis of the complex with visible light. This establishes these complexes as photocatalysts for the production of hydrogen from water in the presence of an electron donor. The production of hydrogen from water using visible light is a means to convert solar energy into chemical energy. Therefore, these complexes are capable of converting solar energy into chemical energy.

REFERENCES

1) "Towards a Supramolecular Photochemistry: Assembly of Molecular Components to Obtain Photochemical Molecular Devices," Balzani, V., Moggi, L., Scandola, F., *Supramolecular Photochemistry,* Balzani, V. ed., D. Reidel, Dordrecht, 1987, 1–28.
2) "Ruthenium(II) Polypyridine Complexes: Photophysics, Photochemistry, Electrochemistry and Chemiluminescence," Juris, A., Balzani, V., Barigelletti, F., Campagna, S., Belser, P., Von Zelewsky, A. *Coord. Chem. Rev.* 1988, 84, 85–277.
3) "Hydrogen Produced from Hydrohalic Acid Solutions by a Two-Electron Mixed-Valence Photocatalyst," Heyduk, A. F., Nocera, D. G. *Science* 2001, 293, 1639–1641.
4) "Photoinitiated Electron Collection in a Mixed-Metal Trimetallic Complex of the Form $\{[(bpy)_2Ru(dpb)]_2 IrCl_2\}(PF_6)_5$ (bpy=2,2'-bipyridine and dpb=2,3-bis(2-pyridyl)benzoquinoxaline Molnar, S. M., Nallas, G. N. A., Bridgewater, J. S., Brewer, K. J., *J. Am. Chem. Soc.* 1994, 116, 5206–5210.
5) "Ruthenium photocatalysts capable of reversibly storing up to four electrons in a single acceptor ligand: a step closer to artificial photosynthesis," Konduri, R.; Ye, H.; MacDonnell, F. M.; Serroni, S.; Campagna, S.; Rajeshwar, K. *Angewandte Chemie,* 2002, 41, 3185–3187.
6) "Photoinduced Multielectron Charge Transfer Processes in Group 8—Platinum Cyanobridged Supramolecular Complexes," Chang, C. C., Pfennig, B., Bocarsly, A. B., *Coord. Chem. Rev.* 2000, 208, 33–45.
7) "Photochemical Image Generation in a Cyanogel System Synthesized from Tetrachloropalladate(II) and the Trimetallic Mixed-Valence Complex $[(CN)_5Fe^{II}-CN-Pt^{IV}(NH_3)_4-NC-Fe^{II}(CN)_5]^{4-}$: Consideration of Photochemical and Dark Mechanistic Pathways of Prussian Blue Formation," Watson, D. F., Wilson, J. L., Bocarsly, A. B., *Inorg. Chem.* 2002, 41, 2408–2416.

We claim:

1. A method of converting radiant energy to chemical energy in the form of hydrogen ($H_2$) from water, comprising the steps of
   exposing said water to
   i) a supramolecular complex comprising
      at least one metal to ligand charge transfer (MLCT) light absorbing metal,
      at least one bridging π-acceptor ligand,
      at least one electron acceptor metal, and
      at least one terminal ligand; and
   ii) a source of radiant energy; and
   producing chemical energy in the form of hydrogen ($H_2$) from said water during said step of exposing.

2. The method of claim 1, wherein said MLCT light absorbing metal is ruthenium.

3. The method of claim 1, wherein said bridging π-acceptor ligand is 2,3'-bis(2-pyridyl)pyrazine.

4. The method of claim 1, wherein said electron acceptor metal is rhodium.

5. The method of claim 1, wherein said terminal ligand is 2,2'-bipyridine.

6. The method of claim 1, wherein said supramolecular complex is $[(bpy)_2Ru(dpp)RhCl_2(dpp)Ru(bpy)_2]^{5+}$.

7. The method of claim 1, wherein said supramolecular complex remains intact during said steps of exposing and producing.

* * * * *